(12) United States Patent
Kreschollek et al.

(10) Patent No.: US 9,018,599 B2
(45) Date of Patent: Apr. 28, 2015

(54) FLUORESCENCE METHOD FOR DETERMINING OCCLUSION IN ENCLOSED SPACES

(75) Inventors: Thomas E. Kreschollek, Clute, TX (US); Rida S. Al Horr, Lake Jackson, TX (US); Steven R. Erskine, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 128 days.

(21) Appl. No.: 13/692,574

(22) PCT Filed: Jun. 3, 2011

(86) PCT No.: PCT/US2011/039109
§ 371 (c)(1),
(2), (4) Date: Mar. 6, 2013

(87) PCT Pub. No.: WO2011/153459
PCT Pub. Date: Dec. 8, 2011

(65) Prior Publication Data
US 2014/0151577 A1    Jun. 5, 2014

Related U.S. Application Data

(60) Provisional application No. 61/351,571, filed on Jun. 4, 2010.

(51) Int. Cl.
*G01J 1/58* (2006.01)
*G01N 21/64* (2006.01)

(52) U.S. Cl.
CPC .................................. *G01N 21/643* (2013.01)

(58) Field of Classification Search
CPC .................................................. G01N 21/6428
USPC ....................................................... 250/459.1
See application file for complete search history.

(56) References Cited

U.S. PATENT DOCUMENTS 7,839,969 B2 *  11/2010  Gallup et al. ................... 378/45

FOREIGN PATENT DOCUMENTS

WO    WO 99/59462    11/1999

* cited by examiner

*Primary Examiner* — David Porta
*Assistant Examiner* — Hugh H Maupin
(74) *Attorney, Agent, or Firm* — Troutman Sanders LLP

(57) ABSTRACT

A method of sensing scale build up on piping exposed to wellbore fluids, which includes the steps of sensing the build up of scale on the wall an injector pipe using fluorescence detection, generating a signal representative of the relative scale build up on injector pipe wall, and communicating that signal to a remote location.

18 Claims, 6 Drawing Sheets

FLUORESCENCE METHOD FOR DETERMINING OCCLUSION IN ENCLOSED SPACES

CROSS-REFERENCE TO RELATED APPLICATIONS AND PRIORITY CLAIM

This application claims priority to PCT application PCT/US2011/039109, filed Jun. 3, 2011 and titled "Fluorescence Method For Determining Occlusion In Enclosed Spaces." This application further claims priority, through the above-referenced PCT application, to U.S. provisional patent application No. 61/351,571, filed Jun. 4, 2010 and having the same title. The foregoing patent applications are hereby incorporated by reference into this application in their entireties.

FIELD OF INVENTION

The invention relates generally to a chemical method for the determination of occlusion due to the build up of sediment in enclosed spaces. More specifically, the invention relates to the fluoro-chemical determination of sediments or scale such as mineral and salt scales in enclosed areas such as piping.

BACKGROUND OF THE INVENTION

Enhanced oil recovery (EOR) has become a fact of modern day oil extraction technology. EOR generally refers to techniques used for increasing the amount of crude oil that can be extracted from an oil field. There are a number of techniques presently used. Drill sites can be treated thermally or with sound to ease the flow of oil from the field to the well head. Chemical injection may be used to create chemical and physical phenomena which facilitate oil flow to the well head. The chemicals may be used to alter capillary pressure within the structures or alter the viscosity of the crude oil or other resident constituents.

By far the most commonly used approach to enhance recovery is gas injection. Supercritical gas is injected by way of injector pipes into oil bearing strata under high pressure. The high pressure gas pushes the oil to the producer pipes at the well head. The pressure of the gas provides two benefits in pushing the gas towards the producer pipes and in lowering the viscosity of the crude oil as the gas mixes with the crude oil. Gases such as $CO_2$ and various natural gases are commonly used in liquid or supercritical form in gas injection.

If viscosity becomes an issue which it often is, the chemistry of the injected $CO_2$ can be altered with the addition of various constituents. One class of constituents commonly added are surfactants. In particular, non-ionic surfactants have been used to provide a favorable viscosity to $CO_2$ and enhance oil production. In application, a surfactant is added to the pressurized flow as the $CO_2$ is injected into the oil field. The surfactants mix with $CO_2$ to create a super critical mixture flowing at high pressure through the injector pipe.

While the mixture of $CO_2$ and surfactants facilitates recovery, the pressurized nature of the mixture causes certain physical phenomena while moving through the injector pipe. One effect of the mixture flowing through the injectors is the deposition of sediment such as mineral and salt scale on the interior walls of the injector pipes. Diluents used in the surfactant mixture such as water, and brine, may also affect the formation of scale.

Given the nature of EOR and the absolute requirements that this processing be run at optimal levels, sediment or scale formation and, in turn, occlusion of injector piping has to be monitored. One monitoring device for monitoring wellbore fluids is disclosed in U.S. Pat. No. 6,880,402. The disclosed device combines a detection device and a manual descaling device but cannot simulate the actual materials which are forming on the injector piping interior wall.

As a result, there is a need for a more effective process useful in detecting the deposition of sediment on piping exposed to wellbore fluids.

SUMMARY OF THE INVENTION

In accordance with one aspect of the invention, there is provided a method of detecting the buildup of sediment on a substrate comprising the steps of sensing the build up of sediment on a substrate through fluorescence, and generating sensed information representative of that sediment build up. Generally the sediment build up on the substrate is sensed by the creation or quenching of a fluorescent agent through a fluorescence probe. The substrate may be floating or fixed adjacent the probe.

In accordance with a further aspect of the invention, there is provided a method of sensing scale build up on piping exposed to wellbore fluids, the method comprising the steps of sensing the build up of scale on the wall of an injector pipe using fluorescence detection, generating a signal representative of the relative scale build up on injector pipe wall, and communicating that signal to a remote location.

DETAILED DESCRIPTION OF THE PREFERRED EMBODIMENTS

Figure 1:
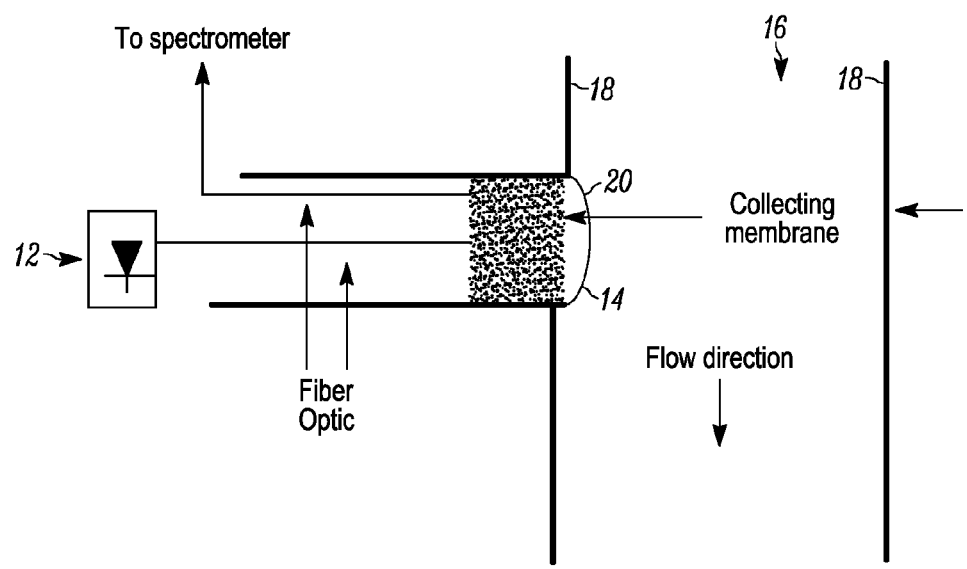
FIG. 1 is a schematic depiction of one environment where the process of the invention may be implemented in accordance with the one embodiment of the invention.

As can be seen in FIG. 1, wherein like parts are designated with like numerals throughout several views, there is shown a fluorescence probe 12 which rests adjacent a collecting membrane 14. The collecting membrane rests within the wall of an injector pipe 16 through which well bore fluids flow. The injection pipe wall 18 is continuous except for an opening 20 into which the collection membrane 14 is placed.

The probe 12 functions to cast light or otherwise illuminate the collection membrane 14. The collection membrane 14 is illuminated preferably through a fiber optic lightsource. Reflected light is returned from the collection membrane to a spectrometer (not shown) where the quality of fluoroluminescence is determined. As noted earlier, one aspect of the invention is a method of determining scale build up through the quenching or creation of a fluorophore which is otherwise impregnated into membrane 14. A second embodiment would be to use a temperature controlled substrate ("cold finger"). This substrate can be heated or cooled to facilitate the formation of solids or scale. In this way, a scale or solids that are fluorescent can be measured directly.

Probe

Any number of probes may be used which facilitate the identification of scale build up upon the internal walls of injector tube. One probe 22 found useful may be seen in FIG. 2. As can be seen, this probe 22 is fiber optic having six fibers 26 gathered around one fiber 28. The exterior six fibers 26 serve to illuminate the target, in this case membrane 20, FIG. 1. The center fiber 28 is generally configured to receive energy or fluorescence reflected from the target. This energy is filtered and passed to a spectrometer through fiber optics.

In addition to this probe any number of other probes may be used such as Raman style probes known to those of skill in the art. Also, the probe may positioned remotely from the target or directly adjacent the channel (as protected) to secure scale build up.

Substrate and Fluorophore

The invention may be used to sense scale build up on the injection pipe side wall. The invention may also comprise a membrane or substrate. Fluorescence is generally measured on the interior surface or wall of the injector pipe. The sediment or scale may also be measured as formed on a substrate or membrane 20 positioned within the injector pipe. One advantage of using a substrate or membrane 20 to determine the formation of scale is that this structure can be removed from the interior portion of the pipe for any number of reasons including examination.

Generally any material may be used to support the measurable buildup of scale or sediment. Preferably the material used to collect sediment or scale closely replicates the interior surface of the injector pipe so as to accurately reflect the formation of sediment or scale on the interior injector pipe wall. To this end, any number of metals and/or metal alloys may be used as a substrate material such as mild steel. Polymeric materials may also be used such as those synthesized from monomers including alkyls, vinyls and vinyl derivatives, acrylates, acrylamides, acrylonitriles, butadienes, alkylacrylates, caprolactones, carbonates, alkylenes, alkylacrylates, alkylene glycols, sulfones, styrenes, and mixtures thereof.

Commonly available polymeric materials include polyvinyl chloride, silicon and fluoropolymers such as tetrafluoroethylene and sulfonated fluoropolymers and copolymers like those sold by DuPont under the Nafion® tradename. Monomers useful in synthesis of the flouorpolymers useful in the invention include fluorinated ethylene and propylene as well as vinyl fluoride, vinylidene fluoride, tetrafluoro, ethylene, hexafluoro propylene, perfluoropropyl vinyl ether, perfluoromethyl vinyl ether, and chlorotrifluoro ethylene and combinations thereof, among others.

Additionally, a fluorophore may also be used with the processes of the invention. Useful fluorophores include those which are sensitive to calcium and potassium ion concentrations such as 3-Octadecanoylimino-7-(diethylamino)-1,2-benzophenoxazine. Other fluorophores found sensitive to fluoride include Bis(fluorodioctylstannyl)methane. Another alternative is to embed solvatochromatic dyes into the polymer membrane or substrate. These dyes would detect the presence of ions more slowly through a shift in the fluorescence or absorbance spectrum. Such dyes include Reichardt's dye and 2,6-Dichloro-4-(2,4,6-triphenyl-1-pyridinio)phenolate.

Processing & Experimental

Preferably, supercritical $CO_2$ is used as the gas of choice for this type of recovery. $CO_2$ in this application is held in liquid form or at a super critical state when pressurized at this level. In order to increase the apparent viscosity of the $CO_2$, a liquid may be injected into the gas flow. The liquid may be any number of compositions with the intent that the resulting mix has a viscosity which allows permeation of strata and displacement of oil from the reservoir. Oil displacement by $CO_2$ generally relies upon phase behavior between the oil and the gas. Factors which effect oil recovery can include reservoir temperature and pressure as well as crude oil composition.

The addition of a liquid to the $CO_2$ is intended to create an emulsion with greater apparent viscosity so that the $CO_2$ will more efficiently sweep the reservoir strata driving crude oil to the well head maximizing recovery.

Any number of liquids can be used consistent with this function. Nonionic surfactants have been found especially useful. Nonionic surfactants are usually organic compounds that are amphiphilic, meaning they contain both hydrophobic groups (alkylated phenol derivatives, fatty acids, long-chain linear alcohols, etc.) and hydrophilic groups (generally ethylene oxide, propylene oxide and/or butylene oxide chains of various lengths), therefore they can be soluble in both organic solvents (non-polar) and polar solvents such as water. For example, the nonionic surfactants of the present disclosure can lower the interfacial tension between carbon dioxide (such as carbon dioxide in a supercritical state) and water. Nonionic surfactants are capable of dissolving in $scCO_2$ in dilute concentrations, where they can help to stabilize carbon dioxide-in-water emulsions and/or foams (referred to herein as "foam"), as discussed herein.

Examples of nonionic surfactants for the present disclosure include, but are not limited to, branched alkylphenol alkoxylates, linear alkylphenol alkoxylates, and branched alkyl alkoxylates. Specific examples of such nonionic surfactants can be found in "$CO_2$-Soluble Surfactants for Improved Mobility Control" authored by Xing et al. (Society of Petroleum Engineers, SPE 129907, presented at the 2010 SPE Improved Oil Recovery Symposium, Tulsa Okla., 24-28 Apr. 2010), which is incorporated herein by reference in its entirety. In one or more embodiments, examples of surfactants useful with the present disclosure can also be found in U.S. Pat. No. 6,686,438 to Beckman and U.S. Pat. No. 5,789, 505 to Wilkinson, and the U.S. Pat. Application entitled "Compositions for Oil Recovery and Methods of Their Use," U.S. patent application Ser. No. 61/196,235, all of which are incorporated herein by reference.

Generally this surfactant may be stored at the site of use in the containment vessel. In storage, the surfactant may be in solution ranging in concentration from about 60 wt-% to 100 wt-%. In use, the surfactant may be thermally treated to enhance recovery and introduced into $CO_2$ flow with an injector quill. While the rate of injection of the liquid into the gas stream may vary, generally, liquid surfactant is injected into the gas stream at a rate creating a concentration of liquid (surfactant) in the wellbore fluid ranging from about 0.1 to 100 gph creating a concentration of liquid (surfactant) in the wellbore fluid ranging from about 100 to 5000.

Figure 2:
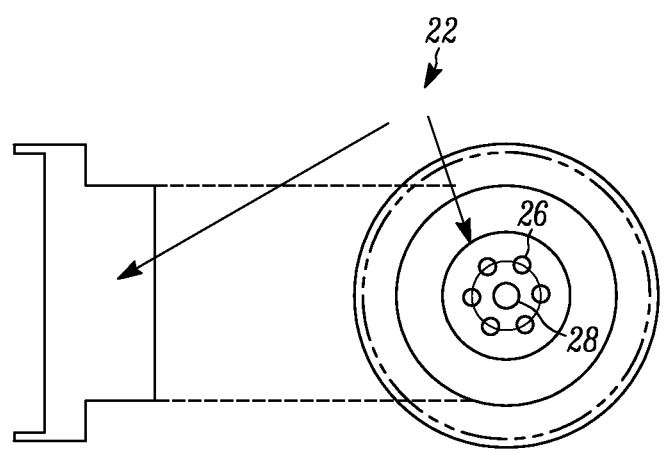
FIG. 2 is a top and corresponding side plan view of a probe which may be used in accordance with one embodiment of the invention.

The method of the invention may be implemented with a probe having holes for an array of fibers, arranged in a 6-around-1 configuration, FIG. 2. In accordance with one embodiment of the invention, the holes were machined into a ⅜" diameter insert fabricated from low expansion coefficient Invar™ alloy. The angle and spacing of the holes is designed to create an intersection at a point several millimeters outside a protective sapphire window surface. The window is brazed to create a high temperature hermetic seal to the Hastelloy C-276 probe body. A clear high temperature epoxy (Tra-Bond F202, TraCon Inc., Bedford, Mass.) was used to retain seven polyimide coated all-silica fibers behind the window and fill the counter-bored cavity of the insert. The insert face was polished flat and scratch free using 0.3 A lapping film on the final pass.

The outer six fibers were coupled with SMA connectors to six light emitting diodes (Part #RL5-B5515, Super Bright LEDs, St. Louis, Mo.) that had a maximum emission at 470 nm. Each LED current is independently controlled by trimmers located adjacent the numbered SMA connectors. A rotary switch and banana connectors allow a selection of internal voltages to accurately set the LED current between 0-40 mA and monitor the power supply.

The light from each source diode was transmitted through a blue additive dichroic filter (P/N Y30-635, Edmund Industrial Optics, Barrington, N.J.) prior to launching into the fiber. 5 mm diameter disks were cut from the 2×2" dielectric stock using a ¼" glass coring tool and saving the core. These disks were mounted in modified fiber optic adapters. This pre-filter is located in the LED Launcher Assembly and removes any non-blue light emitted from the LED.

The center fiber from the probe is filtered with a long-pass filter (P/N OG-530, Edmund Industrial Optics) to remove the blue scattered light but pass the green fluorescence. The 5 mm disk is manufactured as before and mounted into a collimated beam within the Detector Launcher Assembly. The filtered light is transmitted to a low-resolution spectrometer with CCD detection (Model 52000, Ocean Optics Inc., Dunedin, Fla.).

The spectrometer was controlled with software from the same vendor (OOIBase32 version 1.0.0.5, Ocean Optics) which was also used to automate the data collection, (Ocean Optics Spectral Software Operation). In addition to collecting the entire fluorescence spectrum, discrete signals were collected at four places on the emission curve. The data from these discrete wavelengths is automatically saved as a tab-separated variable file. The saved spectra resulted from the averaging of 10 spectra, each collected over a 3-second integration period.

Figure 3:
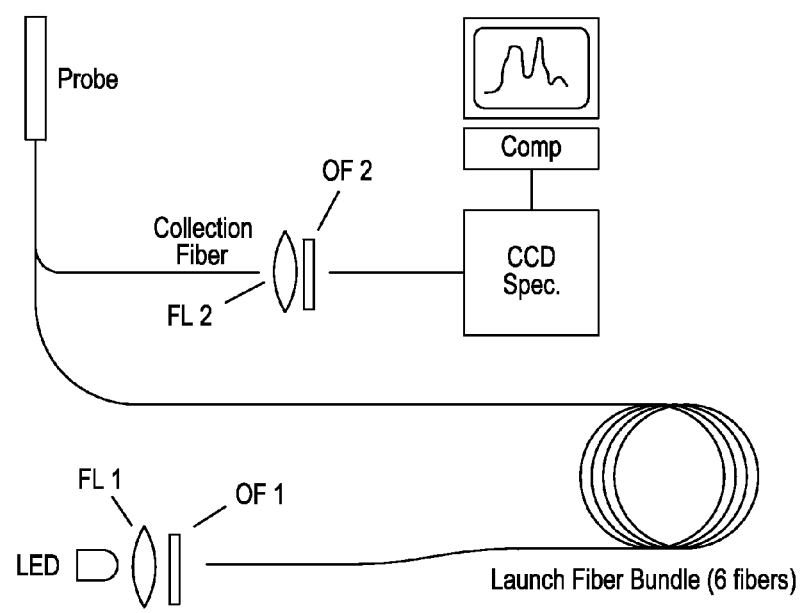
FIG. 3 is a schematic depiction of the optical path and device useful with the invention.

A schematic diagram of the overall optical path and device is shown in FIG. 3. Beginning at the bottom left, LED is a blue light emitting diode (one of 6 shown in diagram), OF 1 (one of six) is the first optical filter used to eliminate non-blue light from each LED, FL 1 (one of six) is the first focusing lens to launch the filtered LED light into each optical fiber (one of six) to launch into the probe.

Light from the probe returns on a single optical fiber to FL 2, a focusing lens to collimate the light, then OF 2, an optical filter used to remove the scattered blue LED light, then a focusing lens (not shown) to launch the light back into the final detector fiber. FL 2, OF 2 and a final focusing lens are mounted in the Detector Launcher Assembly and located in a junction box, which houses the probe and detector fiber connections.

Because the junction box contains no wires or electrical components, it could be located in a classified area near the probe. The CCD Spectrometer is a small dispersion/detection spectrometer that uses an inexpensive room temperature CCD to detect visible light from the fiber. The fluorescence spectrum is acquired, stored, and analyzed on a personal computer.

Figure 4:
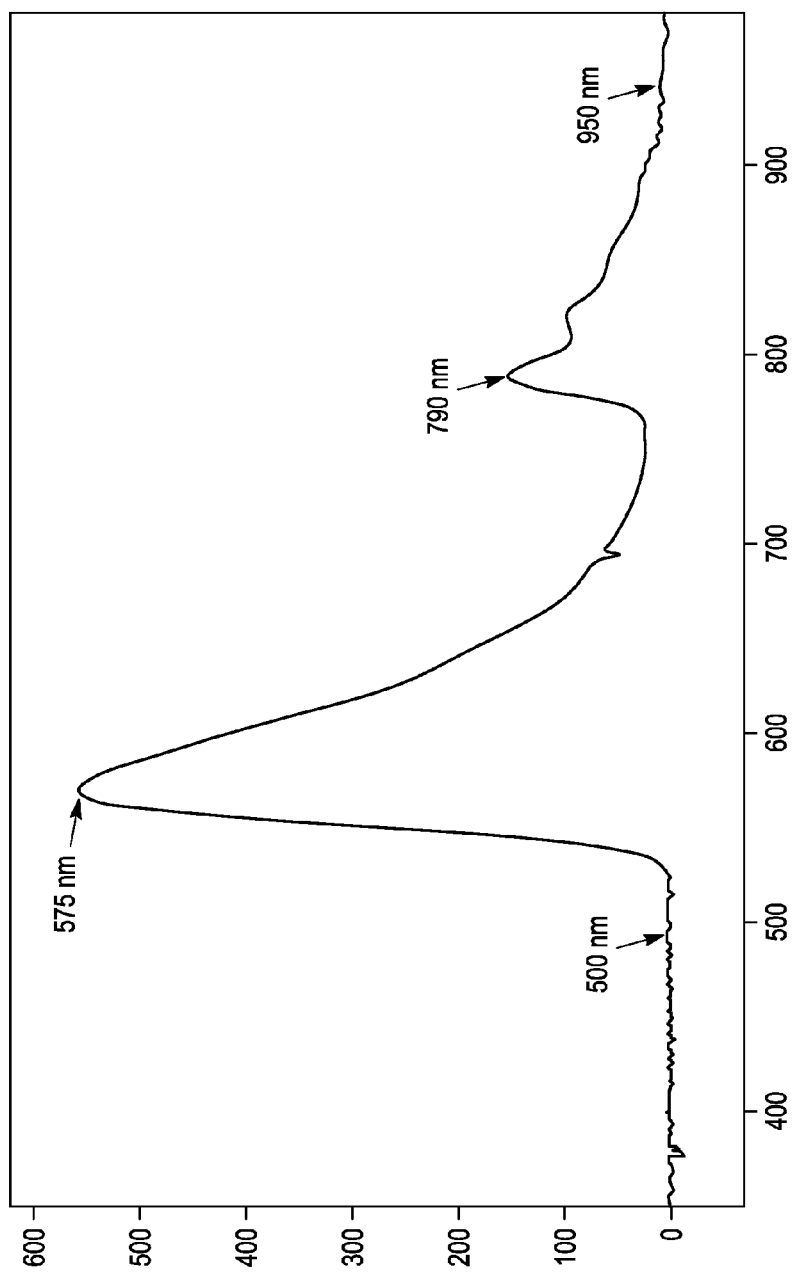
FIG. 4 is a fluorescence spectrum of a polymer coating.

A typical fluorescence spectrum is shown in FIG. 4 with four specific wavelengths marked. Two wavelengths (500 nm and 950 nm) are indicative of baseline level and used to correct fluorescence intensity estimates. The maximum fluorescence signal for the polymer coating is measured at 575 nm. A final wavelength (790 um) provides a representation of the magnitude of the light absorbance due to the solid polymer film of the collector membrane. Any of these discrete wavelengths can be mathematically manipulated or simply plotted with respect to time.

The probe is inserted into the reaction stream through a ½" Swagelok brand "T" fitting through which the cold-finger is inserted. The temperature of the cold finger may vary from about −200 degrees C. to 600 degrees C., preferably from about 0 degrees C. to 300 degrees C. Any number of configurations may be used to cool the substrate including using an actual cooling element as the substrate. The membrane may be heated above the process temperature or cooled below process temperature. The membrane may also be held approximately at the process temperature. Because the external diameter of the probe is ½", the arm of the "T" was bored out such that the probe could be inserted the entire depth of the fitting, allowing the depth of insertion to be adjusted to obtain the maximum signal. The optimal distance between the probe tip and the surface of the cold finger is nominally ⅛" (3 mm). Initially, a simple reference mark was put in place on the probe surface to aid in reproducibly positioning the probe with respect to the distance to the cold finger surface. However, as the Swagelok fitting was tightened and ferrules engaged, the probe would advance slightly, resulting in a position that was not consistent from run to run.

Figure 5:
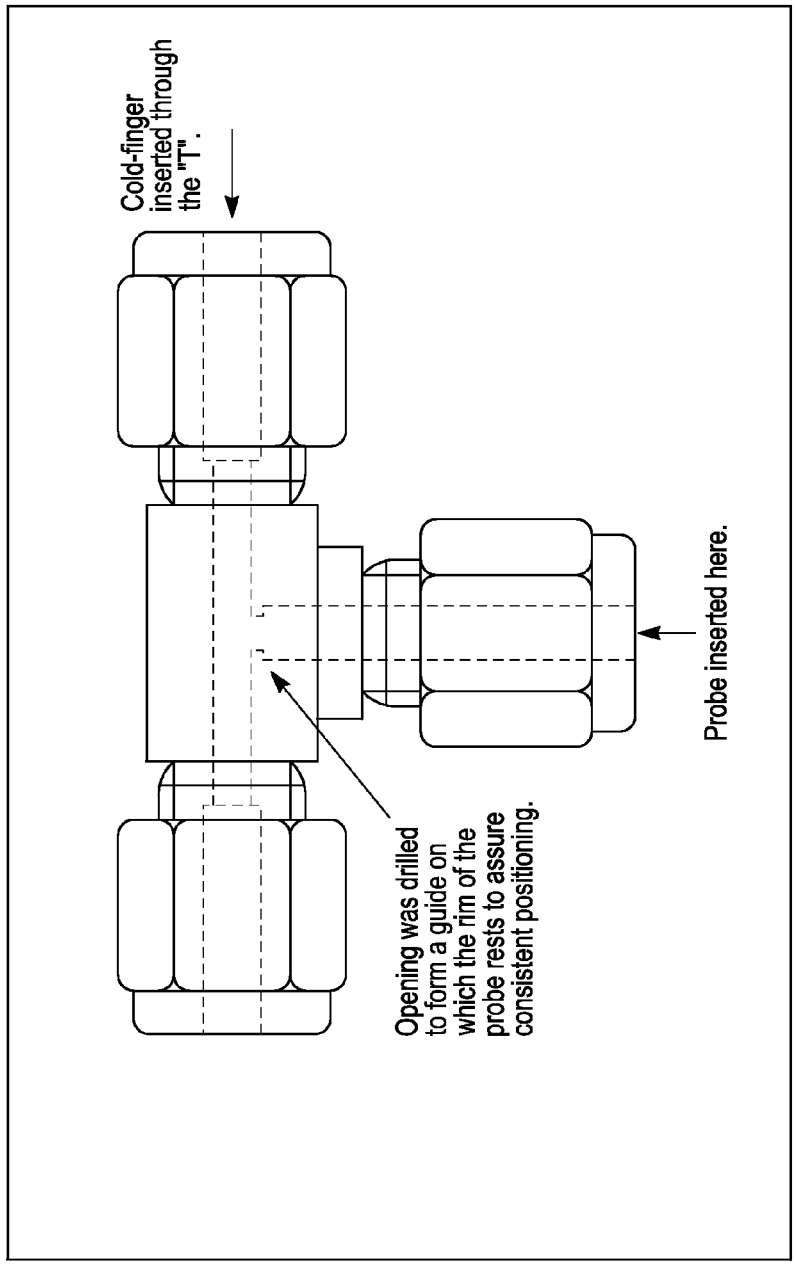
FIG. 5 is a schematic depiction of a modified swagelock T fitting useful with the invention.

A simple solution was implemented by modifying a standard Swagelok "Tee" fitting so that the tip of the probe would rest on a shoulder created by drilling the fitting, as shown in FIG. 5. The shoulder would eliminate any potential positioning error because the distance between probe tip and cold finger is fixed. Repositioning after maintenance is faster and simpler. The fitting was drilled such that the distance between the tip of the probe and the side of the cold finger was approximately ⅛". While the actual distance may not yield the maximum signal, it will yield a reproducible distance and, therefore, consistent signal for a given coating of the solids. Constant initial fluorescence intensity and semi-quantitative results from run to run were achieved.

Another observation that has been made during the initial sets of experiments is that of a decrease in signal during the early phases of a study. This appears only to happen when a fresh cold finger is used. It is speculated that this is due to the initial high reflectivity of a new tube, followed by the roughening of the surface due to the initial layer of solids, resulting a reduction of reflected light.

One can observe that the rate of change at high cold finger temperatures is rather small. This requires a longer experimental run to acquire representative rate data. When acquiring data for cold finger temperatures at 130° C. or less, times of 16 to 24 hours will provide a sufficient amount of data to determine accurate fouling rates. However, at temperatures above 130° C., acquisition times of 36 hours may be necessary to mathematically determine the rate of change of the signal.

Figure 6:
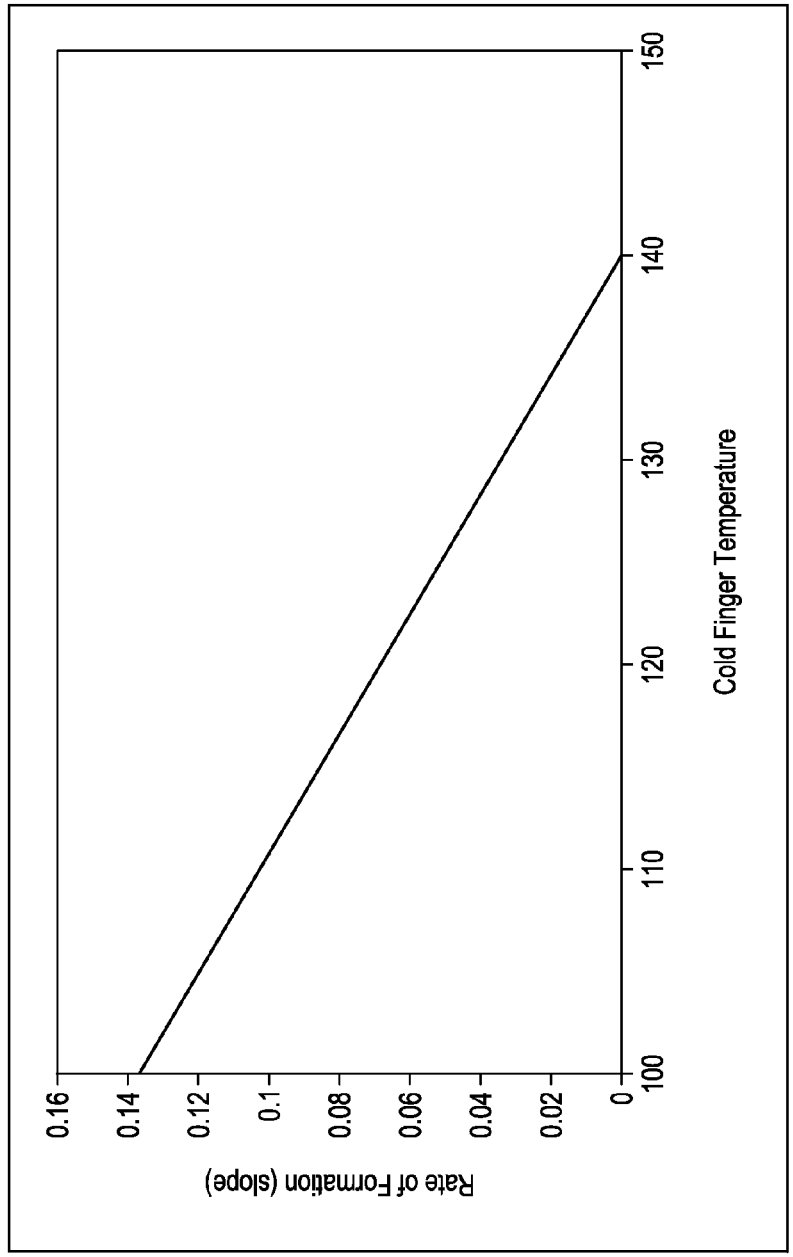
FIG. 6 is a schematic depiction of fluorescence signal versus cold finger temperature.

An analysis of the data can be made by plotting the rate of solids deposition (slope of the fluorescence signal change) as a function of cold finger temperature. This plot can be seen in FIG. 6.

Although the present invention has been described by reference to its preferred embodiment as is disclosed in the specification and drawings above, many more embodiments of the present invention are possible without departing from the invention. Thus, the scope of the invention should be limited only by the appended claims.

The claimed invention is:

1. A method of detecting the buildup of sediment on a substrate, said method comprising the steps of:

a. sensing the buildup of sediment on a substrate through the quenching of a fluorophore fluorescence agent, and
b. generating sensed information representative of that sediment build up.

2. The method of claim 1, wherein the sediment comprises a salt.

3. The method of claim 2, wherein the salt comprises a cation selected from the groups consisting of sodium, calcium, potassium, barium, strontium, magnesium, and mixtures thereof.

4. The method of any of the preceding claims, wherein the buildup of sediment is sensed by a fluorescence probe.

5. The method of claim 4, wherein the sensed sediment is built up on a membrane.

6. The method of claim 5, wherein said membrane is fixed adjacent said probe.

7. The method of claim 6, wherein said membrane floats freely adjacent said probe.

8. The method of claim 7, wherein said membrane comprises a polymeric material.

9. A method of sensing scale build up on piping exposed to wellbore fluids, said method comprising the steps of:
   a. sensing the buildup of scale on the wall of an injector pipe using fluorescence detection;
   b. generating a signal having a magnitude proportionate to the amount of a fluorophore which has been quenched by the scale build up on injector pipe wall; and
   c. communicating that signal to a remote location.

10. The method of claim 9, wherein said scale is forming on the internal wall of said injector pipe.

11. A method as in either claim 9 or 10, wherein the sediment comprises a salt, and said salt comprises a cation selected from the groups consisting of sodium, calcium, potassium, barium, strontium, and mixtures thereof.

12. The method of claim 9, wherein a fluorescence probe senses the sediment build up on a membrane.

13. A method of sensing scale build up on piping exposed to wellbore fluids, said method comprising the steps of:
   a. sensing the buildup of scale on the wall of an injector pipe using fluorescence detection;
   b. generating a signal having a magnitude proportionate to the amount of scale build up on the injector pipe wall, wherein the scale comprises at least one flourophore; and
   c. communicating that signal to a remote location.

14. The method of claim 13, wherein the magnitude of said signal is proportionate to the amount of the at least one fluorophore comprising the scale.

15. The method of claim 13, wherein the fluorophore is deposited on a substrate.

16. The method of claim 15, wherein the substrate comprises material similar to that of the surrounding pipe.

17. The method of claim 15, wherein the substrate comprises material dissimilar to that of the surrounding pipe.

18. The method of claim 15, wherein said substrate is temperature controlled.

* * * * *